United States Patent
Wilson et al.

(10) Patent No.: US 10,039,279 B2
(45) Date of Patent: Aug. 7, 2018

(54) AROMATIC ESTERS FOR CONTROLLING AGRICULTURAL SPRAY DRIFT

(71) Applicants: Stephen L. Wilson, Zionsville, IN (US); Joseph C. Hercamp, New Palestine, IN (US)

(72) Inventors: Stephen L. Wilson, Zionsville, IN (US); Joseph C. Hercamp, New Palestine, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 419 days.

(21) Appl. No.: 13/851,346

(22) Filed: Mar. 27, 2013

(65) Prior Publication Data

US 2013/0260996 A1 Oct. 3, 2013

Related U.S. Application Data

(60) Provisional application No. 61/618,946, filed on Apr. 2, 2012.

(51) Int. Cl.

| | | |
|---|---|---|
| *A01N 25/00* | (2006.01) | |
| *A01N 57/10* | (2006.01) | |
| *A01N 39/04* | (2006.01) | |
| *A01N 37/40* | (2006.01) | |
| *A01N 43/40* | (2006.01) | |
| *A01N 25/04* | (2006.01) | |
| *A01N 25/02* | (2006.01) | |

(52) U.S. Cl.
CPC ............ *A01N 25/00* (2013.01); *A01N 25/02* (2013.01); *A01N 25/04* (2013.01); *A01N 37/40* (2013.01); *A01N 39/04* (2013.01); *A01N 43/40* (2013.01); *A01N 57/10* (2013.01)

(58) Field of Classification Search
CPC ........ A01N 25/00; A01N 25/04; A01N 25/02; A01N 57/10; A01N 39/04; A01N 37/40; A01N 43/40
USPC ........................................................ 504/128
See application file for complete search history.

(56) References Cited

U.S. PATENT DOCUMENTS

| | | | |
|---|---|---|---|
| 6,124,275 A | 9/2000 | Emerson | |
| 2007/0042009 A1* | 2/2007 | Schwarz et al. | ............ 424/400 |
| 2010/0113275 A1 | 5/2010 | Qin et al. | |
| 2012/0065068 A1* | 3/2012 | Downer et al. | ............... 504/128 |

FOREIGN PATENT DOCUMENTS

| | | | | |
|---|---|---|---|---|
| WO | WO 0187064 A1 * | 11/2001 | ............ | A01N 25/02 |
| WO | PCT/US2013/034049 | 4/2014 | | |

OTHER PUBLICATIONS

Horiuchi et al. The floral volatile, methyl benzoate, from snapdragon (*Antirhinum majus*) triggers phytotoxic effects in *Arabidopsis thaliana* Planta 226(1):1-10, 2007.

* cited by examiner

*Primary Examiner* — John Pak
*Assistant Examiner* — Andriae M Holt
(74) *Attorney, Agent, or Firm* — Nicholas M. Kunz

(57) ABSTRACT

Aqueous herbicide concentrates containing an auxinic herbicide, an aromatic ester, and, optionally, a surfactant and uses of aqueous herbicide spray mixtures incorporating such concentrates are described. The aqueous herbicide concentrates described herein include from 20 to 60 weight percent of a water soluble salt of an auxinic herbicide, from 0.1 to 20 weight percent of an aromatic ester, and, optionally, from 0 to 10 weight percent of a surfactant. The aqueous herbicide concentrate is a transparent, homogeneous liquid that forms an emulsion upon dilution into a spray solution.

15 Claims, No Drawings

AROMATIC ESTERS FOR CONTROLLING AGRICULTURAL SPRAY DRIFT

BACKGROUND

Agricultural spraying by economical and available technologies uses hydraulic spray nozzles that inherently produce a wide spectrum of spray droplet sizes. The potential for these spray droplets to drift from the initial, desired site of application is found to be a function of droplet size, with smaller droplets having a higher propensity for off-target movement. Significant research efforts, involving numerous field trials, wind tunnel tests and subsequent generation of predictive math models have led to a greatly enhanced understanding of the relationship between spray droplet size and potential for off-target drift. Although other factors such as meteorological conditions and spray boom height contribute to the potential for drift, spray droplet size distribution has been found to be a predominant factor. Teske et. al. (Teske M. E., Hewitt A. J., Valcore, D. L. 2004. *The Role of Small Droplets in Classifying Drop Size Distributions* ILASS Americas 17$^{th}$ Annual Conference: Arlington Va.) have reported a value of <156 microns ($\mu$m) as the fraction of the spray droplet distribution that contributes to drift. Robert Wolf (Wolf, R. E., *Minimizing Spray Drift*, Dec. 15, 1997, Microsoft® PowerPoint Presentation, available at www.bae.ksu.edu/faculty/wolf/drift.htm, last viewed Sep. 6, 2011) cites a value of <200 $\mu$m as the driftable fraction. A good estimation of droplet size likely to contribute to drift, therefore, is the fraction below about 150 $\mu$m.

The negative consequences of off-target movement can be quite pronounced. Some herbicides have demonstrated very sensitive phytotoxicity to particular plant species at extremely low parts per million (ppm) or even parts per billion (ppb) levels, resulting in restricted applications around sensitive crops, orchards, and residential plantings. For example, the California Dept of Pesticide Regulation imposes buffers of ½-2 miles for propanil containing herbicides applied aerially in the San Joaquin valley.

SUMMARY

Methods and compositions to reduce spray drift are described. The methods to reduce spray drift during the application of an aqueous herbicidal spray mixture include incorporating into an aqueous spray mixture an aqueous herbicidal concentrate. The aqueous herbicidal concentrates include from 0.1 to 20 weight percent of one or more aromatic esters of Formula I or Formula II:

In Formula I, $R^1$ represents a saturated or unsaturated straight or branched chain ($C_1$-$C_8$)alkyl or a saturated or unsaturated straight or branched chain ($C_4$-$C_{12}$) heteroalkyl, and $R^2$ and $R^3$ independently represent hydrogen, hydroxyl, a saturated or unsaturated straight or branched chain ($C_1$-$C_6$)alkyl, or a saturated or unsaturated straight or branched chain ($C_1$-$C_9$) ester. In Formula II, $R^4$ represents a saturated or unsaturated straight or branched chain ($C_1$-$C_8$)alkyl or a saturated or unsaturated straight or branched chain ($C_4$-$C_{12}$) heteroalkyl, and $R^5$ and $R^6$ independently represent hydrogen, hydroxyl, or a saturated or unsaturated straight or branched chain ($C_1$-$C_6$)alkyl. The aqueous herbicidal concentrates also include from 20 to 60 weight percent (ae basis) of at least one auxinic herbicide, and from 0 to 10 weight percent surfactant. The aqueous herbicide concentrates are transparent, homogeneous liquids that form emulsions upon addition to water.

DETAILED DESCRIPTION

Methods and compositions to reduce spray drift are described herein. The methods and compositions reduce the amount of driftable fines of a herbicide spray in both aerial and ground spray applications. The methods include the use of aqueous herbicide spray mixtures incorporating one or more aromatic esters and one or more herbicides. As used herein the term aromatic ester refers to aromatic esters of Formula I and/or Formula II:

Where $R^1$ represents a saturated or unsaturated straight or branched chain ($C_1$-$C_8$)alkyl or a saturated or unsaturated straight or branched chain ($C_4$-$C_{12}$)heteroalkyl (including cyclic analogs), $R^2$ and $R^3$ independently represent hydrogen, hydroxyl, a saturated or unsaturated straight or branched chain ($C_1$-$C_6$)alkyl, or a saturated or unsaturated straight or branched chain ($C_1$-$C_9$)ester, $R^4$ represents a saturated or unsaturated straight or branched chain ($C_1$-$C_8$) alkyl or a saturated or unsaturated straight or branched chain ($C_4$-$C_{12}$)heteroalkyl (including cyclic analogs), and $R^5$ and $R^6$ independently represent hydrogen, hydroxyl, or a saturated or unsaturated straight or branched chain ($C_1$-$C_6$)alkyl. The aqueous herbicidal spray mixtures described herein are created by incorporating into an aqueous spray mixture an aqueous herbicidal concentrate as described herein. The aqueous herbicidal concentrates described herein and used in the aqueous herbicidal spray mixtures described herein include from 0.1 to 20 weight percent of one or more aromatic esters as described by Formula I, Formula II, or mixtures thereof; from 20 to 60 weight percent (acid equivalent (ae) basis) of at least one auxinic herbicide; and from 0 to 10 weight percent surfactant. A 0 to 10 weight percent range for a surfactant in the aqueous herbicidal concentrates described herein is intended to indicate the surfactant is optionally present up to a 10 weight percent level, but that no surfactant is required. The aqueous herbicidal spray mixtures described herein can further include glyphosate and one or more surfactants selected to enhance the herbicidal activity of glyphosate.

Auxinic herbicides useful with the methods and compositions described herein include, for example, clopyralid, triclopyr, 2,4-D, 2,4-DB, MCPA, MCPB, dicamba, aminopyralid, picloram, or mixtures thereof. The methods described herein are most particularly useful for the application of herbicides that are subject to restricted applications around sensitive crops such as spray mixtures containing glyphosate, 2,4-D, triclopyr, dicamba, or mixtures thereof.

Aromatic esters useful with the methods and compositions described herein may be prepared from petroleum derived raw materials or from naturally derived raw materials such as, for example, vegetable, animal, algae, or seed oils, or from combinations of petroleum derived or naturally derived raw materials. Examples of aromatic esters useful with the methods and composition described herein include methyl salicylate, ethyl salicylate, propyl salicylate, isopropyl salicylate, n-butyl salicylate, sec-butyl salicylate, isobutyl salicylate, dibutyl phthalate, dioctyl phthalate, tetrahydrofurfuryl benzoate, benzyl acetate, methyl benzoate, ethyl benzoate, propyl benzoate, and mixtures thereof.

The aqueous herbicide spray mixtures disclosed herein may include insecticides, herbicides, herbicide safeners, or fungicides and the aqueous herbicide spray mixtures may be applied for the control of unwanted plants, fungi, or insects at levels dependent on the concentration of the active ingredient needed to control the target pest.

The aqueous herbicide spray mixtures and aqueous herbicidal concentrates as described herein may be applied in conjunction with one or more other active ingredients to control a wider variety of unwanted plants, fungi, or insects. When used in conjunction with other active ingredients, the presently claimed compositions can be tank mixed with the other active ingredient or active ingredients for spray application, or applied sequentially with the other active ingredient or active ingredients in separate spray applications.

An example of a composition as described herein that may be used in conjunction with another active ingredient comprises an aqueous herbicidal concentrate containing a mixture of an auxinic herbicide such as a water soluble salt of 2,4-D, a water soluble salt of triclopyr, a water soluble salt of dicamba, or mixtures thereof, and an aromatic ester as described herein. Such aqueous herbicidal concentrates may be diluted from 1 to 2000 fold in water at the point of use depending on the agricultural practices and used in spray applications to control weeds in crops.

In some situations, the aqueous herbicide spray mixtures may contain one or more biocides. Biocides may be present in the composition from about 0.001 wt % to about 0.1 wt %. In embodiments, the one or more biocides may be present in the composition at 0.001 wt %, 0.005 wt %, 0.01 wt %, 0.02 wt %, 0.03 wt %, 0.04 wt %, 0.05 wt %, 0.06 wt %, 0.07 wt %, 0.08 wt %, 0.09 wt %, or 0.1 wt %. Examples of biocides include, but are not limited to, bactericides, viricides, fungicides, parasiticides, and the like. Examples of biocide active ingredients include, but are not limited to, phenol compounds (such as phenol, thymol, pentachlorophenol, cresol, and p-chloro-m-xylenol), aldehydic compounds (such as formaldehyde, glutaraldehyde, and paraformaldehyde), acid compounds (such as benzoic acid, sorbic acid, mucochloric acid, and mucobromic acid), esters of p-hydroxybenzoic acid (such as methyl-p-hydroxybenzoate and butyl-p-hydroxybenzoate), rare earth salts, amines, disulfides, heterocyclic compounds (such as thiazinium salts, thiazolinones, and benzimidazoles), quaternary ammonium salts, organic mercury compounds, hexamethylenebiguanide hydrochlorides, benzalkonium chlorides, polyamino propylbiguanides, and 1-2-benzisothiazoline-3-ones. For specific example, an aqueous herbicide spray mixture may comprise Proxel® GXL (Arch Chemicals Inc., Atlanta, Ga.) as a biocide.

Suitable auxinic herbicides for use in the aqueous herbicide spray mixtures and concentrates described herein include, for example, 2,4-D, 2,4-DB, aminopyralid, clopyralid, dicamba, fluoroxypyr, MCPA, MCPB, picloram or triclopyr. Additional herbicides that can be combined with the herbicidal spray mixtures and concentrates as described herein include, but are not limited to, acetochlor, atrazine, benfluralin, cloransulam, cyhalofop, diclosulam, dithiopyr, ethalfluralin, florasulam, flumetsulam, glufosinate, glyphosate, haloxyfop, isoxaben, MSMA, oryzalin, oxyfluorfen, pendimethalin, penoxsulam, propanil, pyroxsulam, quizalofop, tebuthiuron, and trifluralin. Suitable active ingredients for use in the aqueous herbicide spray mixtures and concentrates described herein also include herbicide safeners such as, for example, cloquintocet, flurazole, mefenpyr, and TI-35. Suitable active ingredients that may be used with the aqueous herbicide spray mixtures and concentrates described herein also include insecticides such as, for example, chlorpyrifos, chlorpyrifos-methyl, gamma-cyhalothrin, cypermethrin, deltamethrin, halofenozide, methoxyfenozide, sulfoxaflor, spinosad, spinetoram, and tebufenozide. Additional active ingredients that may be used with the aqueous herbicide spray mixtures and concentrates described herein also include fungicides such as, for example, fenbuconazole, mancozeb, myclobutanil, propiconazole, quinoxyfen, thifluzamide, and zoxamide.

When the aqueous herbicide spray mixtures and concentrates described herein contain water soluble salts of auxinic herbicides and/or include further herbicides such as the water soluble salt of glyphosate, suitable cations contained in these salts include isopropyl ammonium, dimethyl ammonium, triethyl ammonium, monoethanol ammonium, diethanol ammonium, triethanol ammonium, dimethylethanol ammonium, diethyleneglycol ammonium, triisopropanol ammonium, tetramethyl ammonium, tetraethyl ammonium, choline, and potassium. For example, useful 2,4-D salts include the 2,4-D choline salt and the 2,4-D dimethyl ammonium salt, and useful glyphosate salts include the glyphosate dimethyl ammonium salt, the glyphosate isopropyl ammonium salt, and the glyphosate potassium salt.

In an example of an aqueous herbicide spray mixture, the auxinic herbicide is a water soluble salt of 2,4-D (such as 2,4-D choline salt or 2,4-D dimethyl ammonium salt), a water soluble salt of triclopyr (such as triclopyr triethyl ammonium salt), a water soluble salt of dicamba, or mixtures thereof. If glyphosate is included in an aqueous herbicide spray mixture, the glyphosate is a glyphosate dimethyl ammonium salt, a glyphosate isopropyl ammonium salt, or a glyphosate potassium salt. If glyphosate is included in an aqueous herbicide spray mixture, one or more additional surfactants selected to enhance the herbicidal activity of glyphosate can be included. In another example of an aqueous herbicide spray mixture, the auxinic herbicide is 2,4-D choline salt or 2,4-D dimethyl ammonium salt, the glyphosate is glyphosate dimethyl ammonium salt, glyphosate isopropyl ammonium salt, or glyphosate potassium salt, and the aromatic ester is methyl salicylate, ethyl benzoate, propyl benzoate, tetrahydrofurfuryl benzoate, or mixtures thereof. In a further example of an aqueous herbicide spray mixture, the auxinic herbicide is 2,4-D choline salt, the glyphosate is glyphosate dimethyl ammonium salt, and the aromatic ester is methyl salicylate. In an additional example of an aqueous herbicide spray mixture, the auxinic herbicide is triclopyr triethyl ammonium salt, the glyphosate is glyphosate dimethyl ammonium salt, and the aromatic ester is methyl salicylate The optimum spray droplet size depends on the application for which the herbicide composition is used. If droplets are too large, there will be less coverage by the spray; i.e, large droplets will land in certain areas while areas in between will receive little or no spray coverage. The maximum acceptable droplet size may depend on the amount of composition being applied per unit area and the need for uniformity in spray coverage. Smaller droplets provide more even coverage, but are more prone to drift during spraying. Thus, application parameters such as uniformity in spray coverage must be balanced against the tendency for smaller droplets to drift. For example, if it is particularly windy during spraying, larger droplets may be needed to reduce drift, whereas on a calmer day smaller droplets may be acceptable.

In addition to the physical properties of a particular aqueous herbicide composition, spray droplet size may also depend on the spray apparatus, e.g., nozzle size and configuration. The reduction in spray drift may result from a variety of factors including a reduction in the production of fine spray droplets (<150 μm minimum diameter) and an increase in the volume median diameter (VMD) of the spray droplets. In any event, for a given spray apparatus, application, and conditions, and based on the aromatic ester, the median diameter of the plurality of spray droplets created using the compositions and methods described herein is increased above that of a spray composition that does not include the aromatic ester as described herein.

As used herein aqueous herbicide concentrates are solutions containing high concentrations of an aqueous herbicide spray component, i.e., one or more water soluble auxinic herbicide salts and an aromatic ester as defined by Formula I. The aqueous herbicidal concentrates are intended to be diluted to provide aqueous herbicide spray mixtures as described herein. The aqueous herbicide concentrates are transparent, homogeneous liquids that form emulsion upon addition to water. The stability of the emulsions can vary. Some emulsions are stable indefinitely. Other emulsions remain stable for the length of time needed for spray application. An emulsion formed using an aqueous herbicide concentrate as described herein that has separated can typically be reformed by additional agitation.

The aqueous concentrate compositions described herein include from 20 to 60 weight percent (acid equivalent (ae) basis) of one or more water soluble salts of an auxinic herbicide. Additional examples of concentrations for the auxinic herbicide incorporated into the aqueous herbicide concentrate mixture described herein include, from 20 to 55 weight percent of the concentrate mixture, from 20 to 50 weight percent of the concentrate mixture, from 20 to 45 weight percent of the concentrate mixture, from 20 to 40 weight percent of the concentrate mixture, from 20 to 35 weight percent of the concentrate mixture, from 20 to 30 weight percent of the concentrate mixture, and from 20 to 25 weight percent of the concentrate mixture. Further examples of concentrations for the auxinic herbicide incorporated into the aqueous herbicide concentrate mixture described herein include, from 25 to 60 weight percent of the concentrate mixture, from 30 to 60 weight percent of the concentrate mixture, from 35 to 60 weight percent of the concentrate mixture, from 40 to 60 weight percent of the concentrate mixture, from 45 to 60 weight percent of the concentrate mixture, from 50 to 60 weight percent of the concentrate mixture, and from 55 to 60 weight percent of the concentrate mixture. More examples of concentrations for the auxinic herbicide incorporated into the aqueous herbicide concentrate mixture described herein include, from 25 to 55 weight percent of the concentrate mixture, from 30 to 50 weight percent of the concentrate mixture, from 35 to 45 weight percent of the concentrate mixture, and from 38 to 42 weight percent of the concentrate mixture.

The aqueous concentrate compositions described herein include from 0 to 10 weight percent of a surfactant. Additional examples of concentrations for the surfactant incorporated into the aqueous herbicide concentrate mixture described herein include, from 0.01 to 9 weight percent of the concentrate mixture, from 0.01 to 8 weight percent of the concentrate mixture, from 0.01 to 7 weight percent of the concentrate mixture, from 0.01 to 6 weight percent of the concentrate mixture, from 0.01 to 5 weight percent of the concentrate mixture, from 0.01 to 4.5 weight percent of the concentrate mixture, from 0.01 to 4 weight percent of the concentrate mixture, from 0.01 to 3.5 weight percent of the concentrate mixture, from 0.01 to 3 weight percent of the concentrate mixture, from 0.01 to 2.5 weight percent of the concentrate mixture, from 0.01 to 2 weight percent of the concentrate mixture, from 0.01 to 1.5 weight percent of the concentrate mixture, and from 0.05 to 1 weight percent of the concentrate mixture. Further examples of concentrations for the surfactant incorporated into the aqueous herbicide concentrate mixture described herein include, from 0.1 to 9 weight percent of the concentrate mixture, from 0.2 to 9 weight percent of the concentrate mixture, from 0.3 to 9 weight percent of the concentrate mixture, from 0.4 to 9 weight percent of the concentrate mixture, from 0.5 to 9 weight percent of the concentrate mixture, from 0.6 to 9 weight percent of the concentrate mixture, from 0.7 to 9 weight percent of the concentrate mixture, from 0.8 to 9 weight percent of the concentrate mixture, from 0.9 to 9 weight percent of the concentrate mixture, from 1 to 9 weight percent of the concentrate mixture, from 1.5 to 9 weight percent of the concentrate mixture, from 2 to 9 weight percent of the concentrate mixture, from 3 to 9 weight percent of the concentrate mixture, from 4 to 9 weight percent of the concentrate mixture, from 5 to 9 weight percent of the concentrate mixture, from 6 to 9 weight percent of the concentrate mixture, from 7 to 9 weight percent of the concentrate mixture, and from 8 to 9 weight percent of the concentrate mixture. More examples of concentrations for the surfactant incorporated into the aqueous herbicide concentrate mixture described herein include, from 0.2 to 8.5 weight percent of the concentrate mixture, from 0.3 to 8 weight percent of the concentrate mixture, from 0.4 to 7.5 weight percent of the concentrate mixture, from 0.6 to 7 weight percent of the concentrate mixture, from 0.7 to 6.5 weight percent of the concentrate mixture, from 0.8 to 6 weight percent of the concentrate mixture, from 0.9 to 6 weight percent of the concentrate mixture, from 1 to 6 weight percent of the concentrate mixture, from 2 to 5 weight percent of the concentrate mixture, from 2 to 4 weight percent of the concentrate mixture, and from 2 to 3 weight percent of the concentrate mixture.

The aqueous concentrate compositions described herein include from 0.01 to 20 weight percent of an aromatic ester. Additional examples of concentrations for the a aromatic ester incorporated into the aqueous herbicide concentrate mixture described herein include, from 0.01 to 20 weight percent of the concentrate mixture, from 0.01 to 19 weight percent of the concentrate mixture, from 0.01 to 18 weight percent of the concentrate mixture, from 0.01 to 17 weight percent of the concentrate mixture, from 0.01 to 16 weight percent of the concentrate mixture, from 0.01 to 15 weight percent of the concentrate mixture, from 0.01 to 14 weight percent of the concentrate mixture, from 0.01 to 13 weight percent of the concentrate mixture, from 0.01 to 12 weight percent of the concentrate mixture, from 0.01 to 11 weight percent of the concentrate mixture, from 0.01 to 10 weight percent of the concentrate mixture, from 0.01 to 9 weight percent of the concentrate mixture, from 0.01 to 8 weight percent of the concentrate mixture, from 0.01 to 7 weight percent of the concentrate mixture, from 0.01 to 6 weight percent of the concentrate mixture, from 0.01 to 5 weight percent of the concentrate mixture, from 0.01 to 4.5 weight percent of the concentrate mixture, from 0.01 to 4 weight percent of the concentrate mixture, from 0.01 to 3.5 weight percent of the concentrate mixture, from 0.01 to 3 weight percent of the concentrate mixture, from 0.01 to 2.5 weight percent of the concentrate mixture, from 0.01 to 2 weight percent of the concentrate mixture, from 0.01 to 1.5 weight percent of the concentrate mixture, and from 0.05 to 1 weight percent of the concentrate mixture. Further examples of concentrations for the aromatic esters incorporated into the aqueous herbicide concentrate mixture described herein include, from 0.1 to 20 weight percent of the concentrate mixture, from 0.2 to 20 weight percent of the concentrate mixture, from 0.3 to 20 weight percent of the concentrate mixture, from 0.4 to 20 weight percent of the concentrate mixture, from 0.5 to 20 weight percent of the concentrate mixture, from 0.6 to 20 weight percent of the concentrate mixture, from 0.7 to 20 weight percent of the concentrate mixture, from 0.8 to 20 weight percent of the concentrate mixture, from 0.9 to 20 weight percent of the concentrate mixture, from 1 to 20 weight percent of the concentrate mixture, from 1.5 to 20 weight percent of the concentrate mixture, from 2 to 20 weight percent of the concentrate mixture, from 3 to 20 weight percent of the concentrate mixture, from 4 to 20 weight percent of the concentrate mixture, from 5 to 20 weight percent of the concentrate mixture, from 6 to 20 weight percent of the concentrate mixture, from 7 to 20 weight percent of the concentrate mixture, from 8 to 20 weight percent of the concentrate mixture, from 9 to 20 weight percent of the concentrate mixture, from 10 to 20 weight percent of the concentrate mixture, from 12 to 20 weight percent of the concentrate mixture, from 14 to 20 weight percent of the concentrate mixture, from 16 to 20 weight percent of the concentrate mixture, and from 18 to 20 weight percent of the concentrate mixture. More examples of concentrations for the aromatic ester incorporated into the aqueous herbicide concentrate mixture described herein include, from 0.5 to 18 weight percent of the concentrate mixture, from 1 to 16 weight percent of the concentrate mixture, from 2 to 15 weight percent of the concentrate mixture, from 2 to 14 weight percent of the concentrate mixture, from 2 to 12 weight percent of the concentrate mixture, from 2 to 10 weight percent of the concentrate mixture, from 2 to 8 weight percent of the concentrate mixture, from 2 to 6 weight percent of the concentrate mixture, from 2 to 5 weight percent of the concentrate mixture, from 2 to 4 weight percent of the concentrate mixture, and from 2 to 3 weight percent of the concentrate mixture.

The aqueous concentrate compositions can be stored in suitable containers as will be readily recognized by one of skill in the art and can be, for example, solutions, emulsions, or suspensions.

In an example of an aqueous herbicide concentrate composition, the auxinic herbicide is a water soluble salt of 2,4-D (such as 2,4-D choline salt or 2,4-D dimethyl ammonium salt), a water soluble salt of triclopyr (such as triclopyr triethyl ammonium salt), or a water soluble salt of dicamba. In another example of an aqueous concentrate composition, the auxinic herbicide is 2,4-D choline salt, 2,4-D dimethyl ammonium salt, or triclopyr triethyl ammonium salt, and the aromatic ester is methyl salicylate, ethyl benzoate, propyl benzoate, tetrahydrofurfuryl benzoate, or mixtures thereof. In a further example of an aqueous concentrate composition, the auxinic herbicide is 2,4-D choline salt and the aromatic ester is methyl salicylate. In an additional example of an aqueous concentrate composition, the auxinic herbicide is triclopyr triethyl ammonium salt and the aromatic ester is methyl salicylate.

Aqueous spray solutions, containing 2,4-D and glyphosate are prone to incompatibility under certain conditions and concentrations leading to product performance issues and difficulty in using the products, i.e., difficulty with field applications of the products. Incompatibility in spray solutions may be minimized by the use of very small amounts of 2,4-D, such as less than about 3 wt % ae (acid equivalent) relative to the total composition and/or the use of compatibility additives such as is described in U.S. Application Ser. No. 61/523,958, which is incorporated herein by reference.

Optionally, the compositions described herein may contain additional surfactants. The additional surfactants may be anionic, cationic, or nonionic in character. Examples of typical surfactants include alcohol-alkylene oxide addition products, such as tridecyl alcohol-$C_{16}$ ethoxylate; sorbitol esters, such as sorbitol oleate; quaternary amines, such as lauryl trimethylammonium chloride; ethoxylated amines, such as tallowamine ethoxylated; betaine surfactants, such as cocoamidopropyl betaine; fatty acid amidopropyl dimethylamine surfactants such as cocoamidopropyl dimethylamine; alkylpolyglycoside surfactants; polyethylene glycol esters of fatty acids, such as polyethylene glycol stearate; block copolymers of ethylene oxide and propylene oxide; salts of mono and dialkyl phosphate esters; and mixtures thereof. The additional surfactant or mixture of surfactants is usually present at a concentration of from about 0.5 to about 20 weight percent of the formulation.

Additionally, compositions optionally containing one or more additional compatible ingredients are provided herein. These additional ingredients may include, for example, one or more pesticides or other ingredients, which may be dissolved or dispersed in the composition and may be selected from acaricides, bactericides, fungicides, insecticides, herbicides, herbicide safeners, insect attractants, insect repellents, plant activators, plant growth regulators, and synergists. Also, any other additional ingredients providing functional utility such as, for example, dyes, stabilizers, fragrants, viscosity-lowering additives, compatibility agents, and freeze-point depressants may be included in these compositions.

The following Examples are presented to illustrate various aspects of the compositions and methods described herein and should not be construed as limitations to the claims.

EXAMPLES

Example 1: Aqueous Herbicide Concentrates Containing Soluble Aromatic Oils

Aqueous 2,4-D Choline Salt Concentrates

To 9.0 g of an aqueous 2,4-D choline salt concentrate (containing 538 gae/L of 2,4-D choline; prepared by adding 2,4-D acid flake to a 45 wt % aqueous choline hydroxide solution (1.1:1 molar excess of choline hydroxide) with stirring until the 2,4-D acid was completely dissolved and neutralized) was added 1.0 g of an aromatic ester oil chosen from methyl salicylate, ethyl benzoate, and propyl benzoate. After brief agitation, a transparent, homogeneous liquid concentrate resulted. Three aqueous herbicide concentrates (one each containing methyl salicylate, ethyl benzoate, and propyl benzoate) were prepared in this manner.

Aqueous Triclopyr Triethylammonium (TEA) Salt Concentrate

To 9.5 g of an aqueous triclopyr triethylammonium (TEA) salt concentrate (Garlon® 3A; containing 360 gae/L of triclopyr TEA; available from Dow AgroSciences, LLC) was added 0.5 g of methyl salicylate. After brief agitation a clear homogeneous concentrate resulted.

Example 2: Dilution of Aqueous Herbicide Concentrates Containing Soluble Aromatic Oils in Water Approximately 1 g of each of the four concentrates prepared in Example 1 was added to 100 ml of tap water. In all cases, a rich emulsion formed immediately when the clear, homogeneous concentrates were added to the water.

Example 3: Spray Drift Reduction Performance of Herbicide Salt Formulations Containing Aromatic Ester Oils To test the spray drift reduction performance of each organic oil, 400 g spray solutions were prepared by adding 8.8 grams (g) of each of the four herbicide concentrates prepared in Example 1 to 382 g of tap water containing 9.2 g of RoundUp PowerMax® herbicide (540 gae/L of glyphosate potassium (Monsanto; St. Louis, Mo.)). Optionally, ammonium sulfate (AMS, 2 wt %) was included in the spray solution. In all cases, a rich emulsion was formed when the aromatic oil-containing concentrates were added to spray water. As a control, a spray solution containing 2.2 wt % Weedar® 64 (455 gae/L of 2,4-D DMA (Nufarm Inc.; Durham, N.C.)) and 2.3 wt % of RoundUp PowerMax® herbicide in tap water was prepared.

The five spray solutions were sprayed using a Teejet® 8002 flat fan nozzle (Teejet Technologies; Wheaton, Ill.) at 40 psi (276 kiloPascal) and the spray droplet size distribution measurement was performed with a Sympatec Helos/KF high resolution laser diffraction particle sizer with an $R^7$ lens (Sympatec GmbH; Clausthal-Zellerfeld, Germany). The tip of the nozzle was located 12 inches (30.5 centimeters) above the path of the laser beam of the Sympatec particle sizer. The percentage of driftable fines was expressed as the volume percentage of spray droplets below 150 μm volume mean diameter (VMD) as shown in Table 1.

TABLE 1

Spray Droplet Analysis of Herbicide Sprays Containing Aromatic Ester Oils, 2,4-D and Glyphosate, with and without AMS

| Auxinic Herbicide/Aromatic Ester Oil | Volume Percent Driftable Fines <150 μm VMD: no AMS | 2% AMS |
|---|---|---|
| 2,4-D choline/methyl salicylate | 21.8 | 14.8 |
| 2,4-D choline/ethyl benzoate | — | 21.9 |
| 2,4-D choline/propyl benzoate | — | 20.8 |
| triclopyr TEA/methyl salicylate | 21.4 | 23.3 |
| Weedar ® 64/none (control) | 60.8 | — |

The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or method steps may be explicitly mentioned herein; however, other combinations of components and method steps are included, even though not explicitly stated. The term "comprising" and variations thereof as used herein is used synonymously with the term "including" and variations thereof and are open, non-limiting terms.

What is claimed is:

1. A method to reduce spray drift during the application of an aqueous herbicidal spray mixture comprising incorporating into an aqueous spray mixture an aqueous herbicidal concentrate comprising: from 0.1 to 20 weight percent of one or more aromatic esters selected from the group consisting of methyl salicylate, ethyl salicylate, propyl salicylate, isopropyl salicylate, n-butyl-salicylate, sec-butyl salicylate, isobutyl salicylate, dibutyl phthalate, dioctyl phthalate, tetrahydrofurfuryl benzoate and mixtures thereof;
from 20 to 60 weight percent (ae basis) of at least one auxinic herbicide selected from the group consisting of a water soluble salt of 2,4-D, a water soluble salt of triclopyr, a water soluble salt of dicamba and mixtures thereof; and from 0 to 10 weight percent of a surfactant,
wherein the aqueous herbicide concentrate is a transparent, homogeneous liquid and forms an emulsion upon addition to water, and
wherein the aqueous herbicidal concentrate further comprises glyphosate or salts thereof and one or more additional surfactants to enhance the herbicidal activity of glyphosate.

2. The method of claim 1, wherein the auxinic herbicide is a water soluble salt of 2,4-D.

3. The method of claim 1, wherein the auxinic herbicide is 2,4-D choline salt.

4. The method of claim 1, wherein the auxinic herbicide is 2,4-D dimethyl ammonium salt.

5. The method of claim 1, wherein the glyphosate is glyphosate dimethyl ammonium salt, glyphosate isopropyl ammonium salt, or glyphosate potassium salt, the auxinic herbicide is 2,4-D choline salt or 2,4-D dimethyl ammonium salt, and the aromatic ester is methyl salicylate or tetrahydrofurfuryl benzoate.

6. The method of claim 1, wherein the glyphosate is glyphosate dimethyl ammonium salt, the auxinic herbicide is 2,4-D choline salt, and the aromatic ester is methyl salicylate.

7. The method of claim 1, wherein the glyphosate is glyphosate dimethyl ammonium salt, the auxinic herbicide is triclopyr triethyl ammonium salt, and the soluble oil is methyl salicylate.

8. An aqueous herbicidal spray mixture comprising: an aqueous herbicide concentrate composition comprising:
from 0.1 to 20 weight percent of one or more aromatic esters selected from the group consisting of methyl salicylate, ethyl salicylate, propyl salicylate, isopropyl salicylate, n-butyl-salicylate, sec-butyl salicylate, isobutyl salicylate, dibutyl phthalate, dioctyl phthalate, tetrahydrofurfuryl benzoate and mixtures thereof;
from 20 to 60 weight percent (ae basis) of at least one auxinic herbicide selected from the group consisting of a water soluble salt of 2,4-D, a water soluble salt of triclopyr, a water soluble salt of dicamba and mixtures thereof; and
from 0 to 10 weight percent of a surfactant,
wherein the aqueous herbicide concentrate is a transparent, homogeneous liquid and forms an emulsion upon addition to water, and
wherein the aqueous herbicidal concentrate further comprises glyphosate or salts thereof and one or more additional surfactants to enhance the herbicidal activity of glyphosate.

9. The aqueous concentrate composition of claim 8, wherein the auxinic herbicide is a water soluble salt of 2,4-D or a water soluble salt of triclopyr.

10. The aqueous concentrate composition of claim 8, wherein the auxinic herbicide is 2,4-D choline salt.

11. The aqueous concentrate composition of claim 8, wherein the auxinic herbicide is 2,4-D dimethyl ammonium salt.

12. The aqueous concentrate composition of claim 8, wherein the auxinic herbicide is triclopyr triethyl ammonium salt.

13. The aqueous concentrate composition of claim 8, wherein the auxinic herbicide is 2,4-D choline salt, 2,4-D dimethyl ammonium salt, or triclopyr triethyl ammonium salt and the aromatic ester is methyl salicylate, ethyl benzoate, propyl benzoate, tetrahydrofurfuryl benzoate, or mixtures thereof.

14. The aqueous concentrate composition of claim 8, wherein the auxinic herbicide is 2,4-D choline salt and the aromatic ester is methyl salicylate.

15. The aqueous concentrate composition of claim 8, wherein the auxinic herbicide is triclopyr triethyl ammonium salt and the soluble oil is methyl salicylate.

\* \* \* \* \*